United States Patent
Herrington, Jr. et al.

[11] Patent Number: 5,188,612
[45] Date of Patent: Feb. 23, 1993

[54] PHLEBOTOMIST PROTECTOR APPARATUS

[75] Inventors: Eldridge P. Herrington, Jr., West Covina; Richard Spielberg, Alameda, both of Calif.

[73] Assignee: Miles Inc., Elkhart, Ind.

[21] Appl. No.: 783,742

[22] Filed: Oct. 28, 1991

[51] Int. Cl.$^5$ ............................................. A61M 5/32
[52] U.S. Cl. ..................................... 604/192; 128/763
[58] Field of Search ................ 128/760, 763; 604/192, 604/197, 199; 206/364–366

[56] References Cited

U.S. PATENT DOCUMENTS

| | | | |
|---|---|---|---|
| 3,574,306 | 4/1971 | Alden . | |
| 4,232,669 | 11/1980 | Nitshke | 604/192 |
| 4,248,246 | 2/1981 | Ikeda | 128/765 |
| 4,287,988 | 9/1981 | House | 206/365 |
| 4,629,453 | 12/1986 | Cooper | 604/192 |
| 4,717,386 | 1/1988 | Simmons | 604/192 |
| 4,758,229 | 7/1988 | Doerschner | 604/187 |
| 4,767,412 | 8/1988 | Hymanson | 604/192 |
| 4,799,927 | 1/1989 | Davis et al. | 604/192 |
| 4,820,277 | 4/1989 | Norelli | 604/192 |
| 4,832,696 | 5/1989 | Luther et al. | 604/164 |
| 4,846,809 | 7/1989 | Sims | 604/198 |
| 4,892,522 | 1/1990 | Suzuki et al. | 604/192 |
| 4,915,701 | 4/1990 | Halkyard | 604/198 |
| 4,917,243 | 4/1990 | Abrams et al. | 206/365 |
| 4,917,679 | 4/1990 | Kronner | 604/198 |
| 4,944,731 | 7/1990 | Cole | 604/192 |
| 4,966,591 | 10/1990 | Yuen | 604/192 |
| 4,974,728 | 12/1990 | Colton | 206/366 |
| 5,011,475 | 4/1991 | Olson | 604/192 |
| 5,090,564 | 2/1992 | Chimienti | 206/365 |

FOREIGN PATENT DOCUMENTS

| | | |
|---|---|---|
| 0395817 | 11/1990 | European Pat. Off. . |
| 8909076 | 10/1989 | World Int. Prop. O. . |
| WO90/12474 | 12/1989 | World Int. Prop. O. . |

Primary Examiner—Max Hindenburg
Attorney, Agent, or Firm—Elizabeth F. Enayati; James A. Giblin

[57] ABSTRACT

A disposable phlebotomist protector device for enclosing a used needle assembly. The device includes a pair of housing elements each having an end portion and an integral elongate portion. At least one end portion has cannula inset elements for retaining the cannula of a needle assembly when the two housing elements are in an open position relative to each other. The housing elements include locking elements designed to engage the two housing elements to form a closed housing that encloses the needle assembly. One end of the housing includes an aperture when in the closed position for inserting a sample tube that engages with the needle assembly. After the used needle is inserted, the device is closed and secured and sampling completed, the device with the enclosed needle can be disposed.

24 Claims, 3 Drawing Sheets

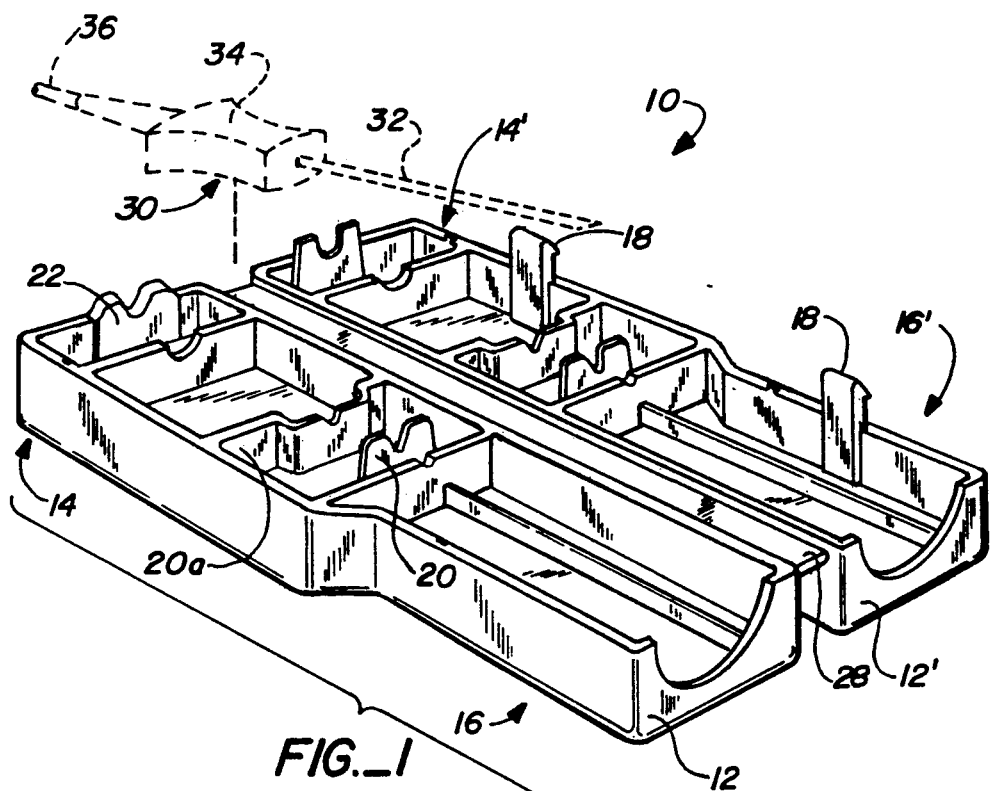
FIG._1
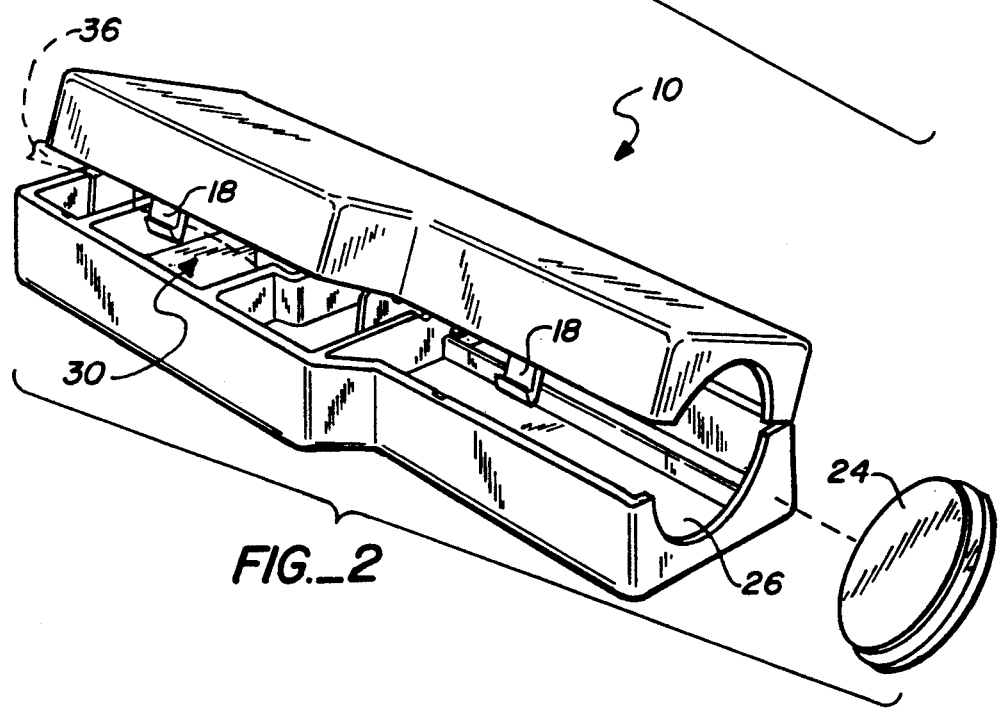
FIG._2

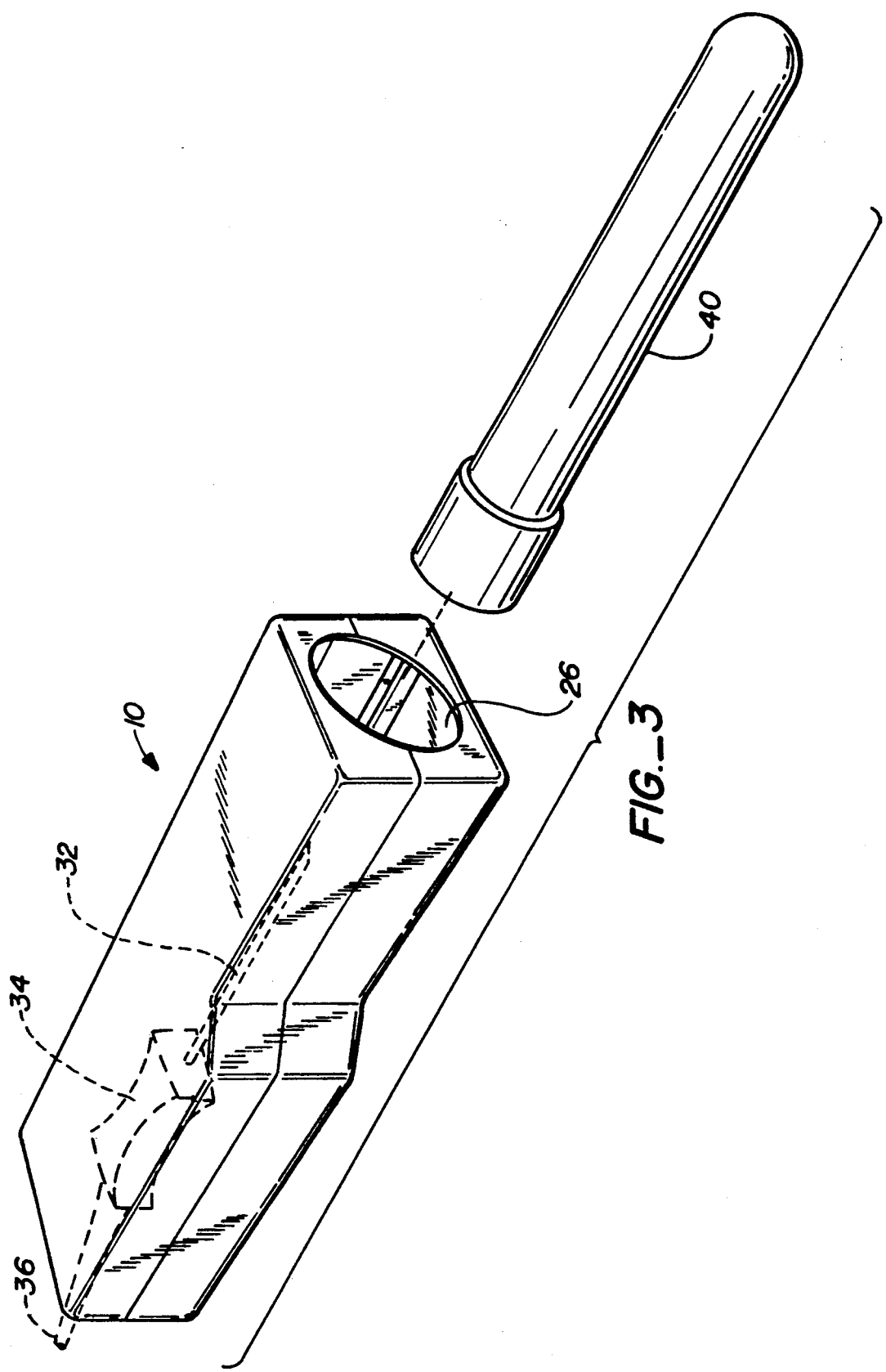
FIG._3

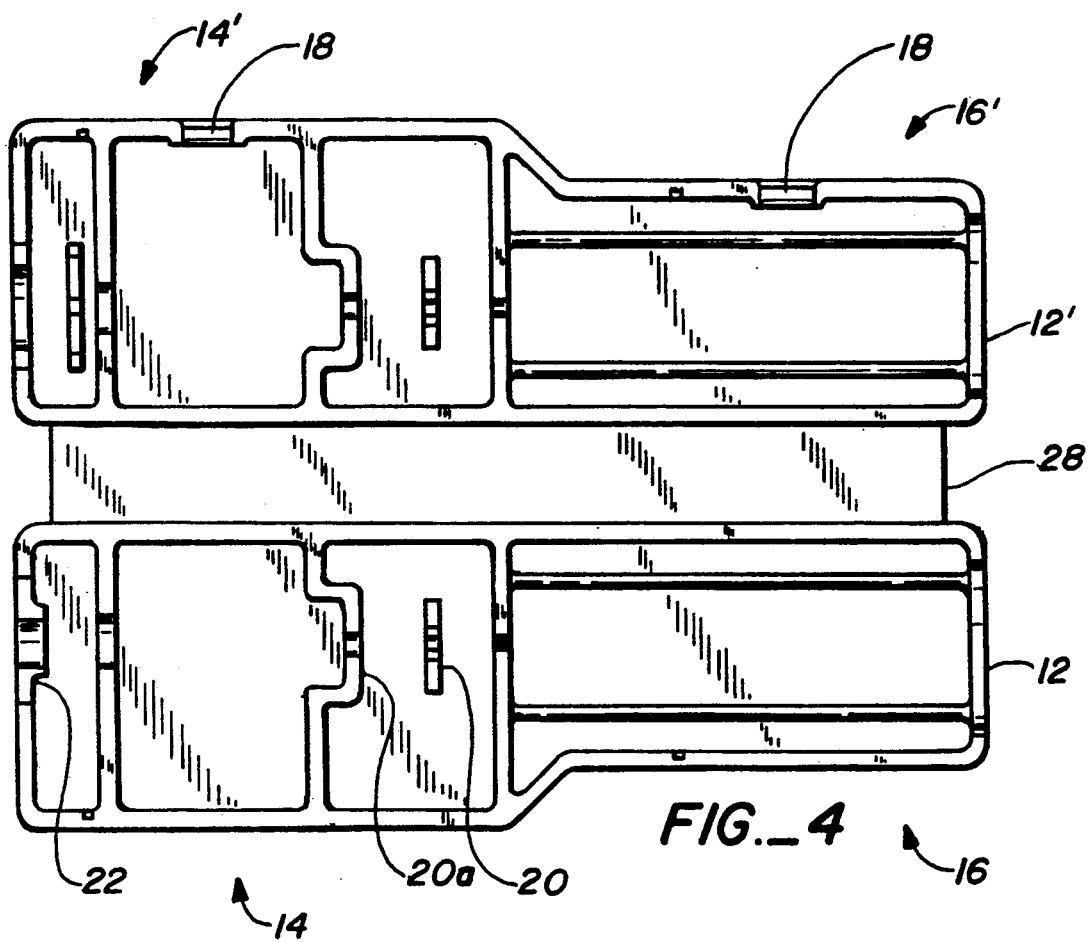

PHLEBOTOMIST PROTECTOR APPARATUS

BACKGROUND OF THE INVENTION

The present invention relates generally to the field of protector devices that protect a phlebotomist and the like from accidental puncture by an exposed needle. Specifically, the invention relates to a needle protector having two engageable halves that enclose the needle of a catheter assembly following use of the needle in a patient.

Phlebotomists represent one sector of the health care industry exposed to risks arising from accidental skin puncture by used needles. Accidental skin puncture can introduce viruses, bacteria, and other elements present in the circulatory system. An increased awareness of the hazards of skin punctures has arisen with the advent of AIDS in the health care sector, since AIDS is reportedly transmitted via the circulatory system.

In normal practice, using a terminal needle a phlebotomist draws blood from an individual to deliver blood into an attached syringe, directly into sampling tubes, or via a catheter assembly to collection bags for storage and subsequent use. Once the blood is drawn and the phlebotomist removes the needle from the patient's arm, there is risk of puncture from the exposed contaminated needle. During subsequent blood sampling, a phlebotomist risks needle puncture while inserting a vacutainer on the receiving end of the same or an in-line needle assembly. A phlebotomist also risks accidental puncture while replacing the old needle cover.

Exemplary art protection devices, consist of a hollow cylinder having a large top flange designed to protect the phlebotomist from impalement. The needle point is guided and inserted into a small hole in the flange and the needle hub is snapped into place. Thus positioned, that pointed end of the needle extends into the hollow cylinder. A vacutainer, or other similar sample tube, can then be inserted into the opposite end of the device so that the needle point punctures the vacutainer stopper and a blood sample drawn from the patient is directed into the vacutainer. The sampling procedure may then be repeated, replacing the vacutainer for multiple sampling, or the entire device is discarded. This disposable device is then used to retain/contain the needle assembly for disposal.

However, with such a design, it is difficult to insert the needle tip into the entry hole of the flange. The phlebotomist who does not have keen eyesight may take a long time in positioning the needle into the flange, or may miss the flange and receive a skin puncture. There is also risk of damaging the tip of the needle if the phlebotomist does miss the flange opening. The damaged needle tip may result in impaired flow through the tip, and other undesirable results.

Thus, there is a need for a protection device that protects a phlebotomist from puncture by a used needle. Such a device may be utilized prior to sampling, for safe transport of the exposed needle, for sampling prior to disposal of the used needle, and for containing the used needle for disposal.

SUMMARY OF THE INVENTION

The present invention generally is a protection device for shielding the user of a needle assembly or catheter assembly from accidental puncture by a used exposed needle. In practice, the disclosed protection device is for use by phlebotomists and other health care practitioners who use or are exposed to needles used in blood sampling or collection.

Generally, the inventive apparatus includes an opposed pair of complementary housing elements that form a substantially hollow housing when in a closed position. Each housing element has an end section and an integral elongate section. At least one housing element includes a locking element for holding the two housing elements together in a closed position.

The end section of at least one housing element primarily includes a cannula inset consisting of a fitted notch to tightly engage the cannula of a needle or catheter assembly. The cannula inset is located in the end section such that the cannula extends into the elongate portion. One end of the elongate portion has an aperture, which is defined when the two halves are positioned together. This aperture is a predetermined diameter to enable insertion of a sample tube, such as a vacutainer.

In a preferred form of the invention, the end section also includes a handle inset element that is adapted to receive a needle handle (hub). In a form of the apparatus used with catheter assemblies, the end section also includes a tube inset element for supporting and receiving the catheter tubing.

Preferably, the two housing elements are connected along opposing edges by a hinge-type arrangement, although other forms of connection may be used. Alternatively, there may be no connection between the two housing elements, and each element includes locking elements to secure the two previously-disconnected housing elements in a closed position.

In practicing a preferred form of the invention, the housing elements are laid out in an open position. A terminal or in-line needle assembly may be positioned in either housing element, since the two elements of the pair are complementary. The two pairs are then closed and the locking elements essentially lock the two pieces together. Preferably, the housing cannot be reopened once it is locked.

In that configuration, the catheter tubing extends out of one end of the closed housing, the needle assembly is contained completely within the closed housing, and the aperture at the other end of the closed housing enables introduction of a sampling tube, such as a vacutainer, into the hollow elongate portion of the housing. When the vacutainer is positioned in the elongate portion, the rubber stopper of the vacutainer engages the needle.

BRIEF DESCRIPTION OF THE DRAWINGS

The invention is further described in conjunction with the figures in which:

FIG. 1 shows a perspective view of the apparatus of the present invention with the two housing elements in an open position;

FIG. 2 shows a perspective view of the apparatus of FIG. 1 in a partially closed position;

FIG. 3 shows a perspective view of the apparatus of FIGS. 1-2 in its closed position, with a terminal needle assembly enclosed therein and a sampling tube being inserted into the aperture; and FIG. 4 shows a top plan view of the apparatus of FIG. 1 in its open position.

Like elements in each figure have the same reference number.

DETAILED DESCRIPTION OF THE INVENTION

The present device described herein consists of two complementary opposing housing elements which, when joined together, form a housing apparatus for containing a used needle assembly. Each housing element may have a plurality of cannula inset elements for securely retaining the cannula while the other housing element is positioned over the first half to form a closed housing. The needle assembly and housing may then be discarded.

Referring now to FIG. 1, the inventive apparatus 10 includes two complementary housing elements 12, 12'. Each element 12, 12' includes an end portion 14 and an elongate portion 16. As shown, the end portions 14, 14' may have several insets for different portions of the needle assembly 30. The number and type of insets may vary depending on manufacturing, cost, materials, the type of cannula or needle assembly for which the device is built, and other such considerations.

In the illustrated embodiment, the end portion 14 includes two cannula insets 20, 20a, and a tubing inset 22. The two cannula insets 20, 20a assure that the cannula 32 remains securely fixed and aligned in the housing element 12. One of these insets 20, 20a may be designed to snap-fit the cannula, while another of the insets may be designed to merely receive, without retaining, the cannula. As described in further detail below, alignment of the cannula 32 assures that the cannula 32 is accessible by a sampling tube (element 40 shown in FIG. 3) introduced into the closed housing.

In alternative embodiments, the end portion 12 may include only a single cannula inset element 20. If the needle assembly 30 is part of a catheter set, the end portion 14 includes a tubing inset 22, or a notch in the end panel of the housing element that retains and positions the tubing 36 to enable the two housing elements 14, 14' to close without interference from the tubing 36. If the needle assembly 30 is part of a cannula/syringe assembly the end portion 14 may include a recessed portion for receiving the syringe.

In a preferred form of the invention the two housing elements 12, 12' include complementary insets, or retaining elements, so that the phlebotomist can position the needle assembly within either housing element when they are in the open position relative to each other. In an alternative embodiment, only one housing element has the inset elements, while the opposing element is substantially hollow yet still fits with the other housing element to form a hollow closed housing.

An important aspect of the present invention is that the used needle assembly is layed into the end portion of the housing element. As discussed above, prior art systems require that the user position the cannula tip into a small opening. By contrast, in each embodiment of the present invention, the needle assembly is place onto the inset elements and secured in these inset elements. In the embodiment having a tubular elongate portion, the end of the tube that is attached to the end portion of the housing element has a large enough opening that the phlebotomist has a minimal chance of self-puncture.

The end portions 14, 14' may also include a needle handle inset 38 which is essentially a recessed portion for receiving the needle handle 34. This portion may be configured to accept certain specified types of needle handles, or may be configured as a universal recess to accept any type of needle handle. This inset 38 may be omitted for needle assemblies that do not include a needle handle. Further, the end portion 14 may be configured to accept a syringe or other similar sampling device. In that instance, the apparatus would include a syringe inset in place of the illustrated tube inset 22.

Each housing element may include an integral elongate portion 16, 16'. In the illustrated embodiment, the elongate portion 16 is substantially hollow and includes a recess at one end. The recesses of the complementary pair of housing elements form an aperture when the two housing elements are in the closed position.

In an alternative embodiment, the elongate portion 16 is a substantially hollow tube that is fixed at one end to one of the housing elements. In practicing that form of the invention, the needle assembly 30 is positioned in the end portion in such a manner that the cannula 32 of the needle assembly 30 is initially positioned within the elongate tube portion 16. Once the cannula 32 and other elements of the needle assembly 30 are positioned in the end portion with the attached elongate tube portion, the other housing element is brought into position to engage with that housing element and form the closed housing. For this embodiment, the attached end of the tube portion is open and has a opening to make insertion of the cannula relatively safe and easy for the user.

After the needle assembly 30 is affixed in the housing element 12, the opposing housing element 12' is brought into position and secured to form a closed housing enclosing the needle assembly, as shown in FIG. 2. The lock elements 18 are used to keep the two housing elements in position. Preferably, once the two housing elements are closed, they cannot readily be reopened, or can be opened only by use of a specially designed key.

As shown in FIG. 3, once needle assembly 34 is secured and the housing elements are secured together forming the closed housing, a sample tube 40, such as a vacutainer, may be introduced through the aperture 26 to engage the cannula 32. The elongate portion 16 generally has a length at least equal to the length of the enclosed cannula. This is so that the user of the device is not impaled by a protruding needle tip.

Preferably, the elongate portion is substantially longer than the cannula length. It is important that the elongate portion is not so long that a sample tube inserted through the aperture 26 does not reach the enclosed cannula. Ideally, the length minimizes the penetration length of the cannula into the sample tube, while being long enough to reduce the risk of a user reaching the needle through the aperture with his/her finger.

In one form of the inventive system, a cap 24 is provided to seal the aperture 26. The cap 24 may be preattached or of any other type generally commercially available. The cap 24 may be an insert-type cap, designed to be inserted into the aperture 26, or it may be a cover-type cap, designed to enclose the top of the elongated portion of the closed housing. Alternatively, the inventive system may be made without an aperture and subsequently used solely for disposing of used needle or catheter assemblies.

As shown in FIGS. 1 and 4, the housing elements 12, 12' may be connected by a hinging element 28. The hinging element 28 may be a strip of flexible plastic or the like that keeps the two housing elements 12, 12' joined when in the open position. Alternatively, the two housing elements may be manufactured from a single piece of foldable material such that the two housing elements are essentially a single piece. In either of these embodiments, either or both housing elements may have one or more lock elements 18 to secure the two housing elements in a closed position. Preferably, the lock elements 18 are of the type that substantially permanently secures the one housing element to another, to prevent the housing from opening once the used needle or catheter assembly is positioned therein.

In an alternative embodiment, the two housing elements 12, 12' are two distinct and separate pieces. In that embodiment, both housing elements 12, 12' must include lock elements in order to assure that the elements are securely fastened in the closed position.

In practicing the inventive method using the protector device, the phlebotomist draws blood from a donor or patient using standard techniques and any commercially available catheter or needle assembly. Once the blood collection is complete, the phlebotomist lays the two housing elements 12, 12' on a flat surface or in the user's hand, in their open position relative to each other. In this position, the inset elements are exposed and the needle assembly can be positioned in the appropriate end portion of a housing element. At this point the phlebotomist may clamp off any tubing that may be leading from the needle assembly to a blood bag or other collection assembly.

Next, the phlebotomist places the needle handle 34 in the needle handle retaining portion 38 of the end portion 14 of either housing element. The cannula 32 is then pressed into the cannula inset 20 to snap into place. If the phlebotomist is using a catheter or needle assembly having tubing, the tubing 36 is generally positioned in the tubing inset 22, followed by the needle handle in the handle inset 38, and finally the cannula 32 is placed in the cannula inset 20. Once properly positioned, the tubing and cannula are essentially parallel to the base of the device 10.

Next, an empty sample tube 40, such as a vacutainer, is inserted into the aperture 26 at the end of the elongate portion 16 of the closed housing. The tube 40 is inserted such that the puncturable stopper 42 tip portion of the sample tube 40 is inserted toward the exposed cannula tip. If a clamp was used to stop the blood flow to and from a blood collection assembly, the clamp or valve may be opened to allow blood flow from storage into the sample tube. After the sample tube 40 is filled, the blood flow is again stopped, and the tube 40 removed from the housing 10. This process is repeated until the desired number of sample tubes are filled.

Upon completion of sampling, the donor tubing at the base of the needle is sealed and the entire closed housing containing the needle assembly is disposed of in a standard manner. The aperture 26 may be closed using the disclosed cap 24 prior to disposal.

The invention may be embodied in other specific forms without departing from the spirit or essential characteristics thereof. The present embodiments are therefore to the considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. Apparatus for enclosing a used needle assembly, having a cannula with a needle handle and tubing attached thereto, said apparatus comprising:
   an opposed pair of complementary housing elements that form a substantially hollow housing when in an engaged, closed position; each said housing element including
   A. an end section having:
      (i) a tubing inset element for receiving said tubing,
      (ii) handle receiving means, distal to said tubing inset element, for receiving said needle handle, and
      (iii) at least one cannula inset means for engaging at least a portion of said cannula, and
   B. an elongate section, integral at one end with said end section, for receiving said cannula once it is engaged in said cannula inset means, said elongate section including a substantially concave portion at the other end that, when said pair of housing elements are joined in said closed position, defines an aperture of a predetermined area, whereby at least one of said housing elements includes a lock element for securing one said housing element to said opposing complementary housing element.

2. The apparatus of claim 1 wherein said housing elements are in hinged communication along opposing edges.

3. The apparatus of claim 1 wherein said aperture enables introduction of a sampling tube into said elongate section for engaging with said cannula.

4. The apparatus of claim 1 wherein said opposing pair of housing elements are substantially permanently engaged when in a closed position.

5. The apparatus of claim 1 further comprising a cap adapted to close said aperture.

6. The system of claim 1 wherein said elongate section and said cannula are at least equal in length.

7. The system of claim 6 wherein said elongate section has a length greater than that of said cannula.

8. A system for protecting phlebotomists from needle puncture after using a needle assembly, having a cannula and a needle handle attached thereto, said system comprising:
   an opposed pair of complementary housing elements that form a substantially hollow housing when in an engaged, closed position; each said housing element including
   an end section having at least one securing means, one of said securing means being a cannula inset means for engaging at least a portion of said cannula; and
   an elongate section, integral at one end with said end section, for receiving said cannula once it is engaged in said cannula inset means, said elongate section including a substantially concave portion at the other end that, when said pair of housing elements are joined in said closed position, defines an aperture of predetermined area, and
   at least one of said housing element including a lock element for securing one said housing element to said opposing complementary housing element in said closed position.

9. The system of claim 8 further comprising handle receiving means, distal to said cannula inset means, for receiving a needle handle attached to said cannula.

10. The system of claim 8 further comprising a tubing inset element, distal to said cannula and said needle handle, for receiving tubing attached to said needle handle.

11. The system of claim 8 wherein said housing elements define an open position during which said cannula may be secured in one said securing means of one said housing element, and define said closed position during which said cannula is enclosed within a space defined by said elongate portions of said housing elements.

12. The system of claim 8 wherein said area of said aperture is of a size that enables introduction of a sampling tube into said elongate section to engage with said cannula.

13. The system of claim 8 wherein said elongate section and said cannula are at least equal in length.

14. The system of claim 13 wherein said elongate section has a length greater than that of said cannula.

15. Apparatus for protecting phlebotomists from needle puncture after using a needle assembly, having a cannula and a needle handle attached thereto, comprising:
an opposed pair of elongate housing elements that form a substantially hollow housing when in an engaged, closed position, at least one of said housing elements including:
   A. an end section having at least one cannula inset means for engaging at least a portion of said cannula, and
   B. an elongate section, integral at one end with said end section, for receiving said cannula once it is engaged in said cannula inset means, said elongate section including a substantially concave portion at the other end that, when said pair of housing elements are joined in said closed position, defines an aperture of predetermined area,
whereby at least one of said housing elements includes a lock element for securing said housing elements to each other in said closed position.

16. The system of claim 15 further comprising handle receiving means, distal to said cannula inset means, for receiving said needle handle.

17. The system of claim 15 further comprising a tubing inset element, distal to said cannula and said needle handle, for receiving tubing attached to said needle handle.

18. The system of claim 15 wherein said housing elements define an open position during which said cannula may be secured in said cannula inset element of one said housing element, and define said closed position during which said cannula is enclosed within a space defined by said complementary pair of housing elements.

19. The system of claim 15 wherein said area of said aperture is such that it enables introduction of a sampling tube into said elongate section to engage with said cannula.

20. The system of claim 15 wherein said elongate section and said cannula are at least equal in length.

21. The system of claim 20 wherein said elongate section has a length grater than that of said cannula.

22. The system of claim 15 wherein said end portion further comprises a syringe inset.

23. A method of collecting blood samples, comprising the sequential steps of:
   A. drawing and storing blood from a patient, using a needle assembly having a cannula with an attached needle handle and tubing enabling blood flow through said needle to a storage element;
   B. securing said needle assembly in said apparatus of claim 1, while said apparatus is in a first, open position;
   C. retaining said assembly within said apparatus by positioning said apparatus in a second, closed position;
   D. sliding a blood sampling tube into said aperture of said apparatus to engage said cannula; and
   E. dispersing blood from said storage element into said blood sampling tube.

24. The method of claim 23 further comprising the steps of, following said dispersing step:
   A. removing said blood sampling tube; and
   B. disposing of said needle assembly contained within said apparatus.

* * * * *